United States Patent [19]
Vadas et al.

[11] Patent Number: 5,591,427
[45] Date of Patent: Jan. 7, 1997

[54] HUMAN INTERLEUKIN-3(IL-3) VARIANTS AND THEIR USE TO PROMOTE OR ANTAGONIZE IL-3-MEDIATED PROCESSES

[75] Inventors: Mathew A. Vadas; Angel F. Lopez; Mary F. Shannon, all of South Australia, Australia

[73] Assignee: Medvet Science Pty. Ltd., South Australia, Australia

[21] Appl. No.: 211,524

[22] PCT Filed: Oct. 7, 1992

[86] PCT No.: PCT/AU92/00535

§ 371 Date: Jun. 20, 1994

§ 102(e) Date: Jun. 20, 1994

[87] PCT Pub. No.: WO93/07171

PCT Pub. Date: Apr. 15, 1993

[30] Foreign Application Priority Data

Oct. 7, 1979 [AU] Australia .............................. PK8742/91

[51] Int. Cl.⁶ .......................... A61K 38/21; C07K 14/54; C12N 15/24

[52] U.S. Cl. ...................... 424/85.2; 530/351; 435/69.52
[58] Field of Search .................................. 530/350, 351; 424/85.2; 435/69.52

[56] References Cited

FOREIGN PATENT DOCUMENTS

| 14294 | 2/1988 | Australia . |
| 60960 | 8/1990 | Australia . |
| 0413383 | 2/1990 | European Pat. Off. ........ C12N 15/27 |
| 88/0616 | 8/1988 | WIPO ............................ C07K 13/00 |

OTHER PUBLICATIONS

Burger, H., et al. (1990) *Blood* 76(11):2229–34.

*Primary Examiner*—David L. Fitzgerald
*Attorney, Agent, or Firm*—Felfe & Lynch

[57] ABSTRACT

This invention relates to human IL-3 variants. The human IL-3 variants are used in pharmaceutical compositions, in methods for modulating proliferation, differentiation or functional activation of cells expressing the IL-3 receptor, and in methods of treatment.

19 Claims, 8 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 1:

ATATCAAGGC CGGTGACTG                                           19

( 2 ) INFORMATION FOR SEQ ID NO: 2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 2:

TATAGTTCCG GCCACTGAC                                           19

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 3:

CAGTCACCGG CCTTGATAT                                           19

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 4:

TTCTATCTGG TGACCCTTGA G                                       21

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 5:

AAGATAGACC ACTGGGAACT C 21

( 2 ) INFORMATION FOR SEQ ID NO: 6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 6:

CTCAAGGGTC ACCAGATAGA A 21

HUMAN INTERLEUKIN-3(IL-3) VARIANTS AND THEIR USE TO PROMOTE OR ANTAGONIZE IL-3-MEDIATED PROCESSES

This invention relates to variants and mutants of human interleukin-3 (hIL-3), and in particular it relates to hIL-3 va sequence of wild-type hIL-3 is varied in order to obtain useful changes in activity, particularly in binding to IL-3 receptors and in biological function.

Human IL-3 is a T-cell-derived glycoprotein of Mr 23–30 kd which promotes the proliferation and differentiation of haemopoietic progenitor cells, including megakaryocytes, eosinophils, basophils, neutrophils, monocytes and T-lymphocytes. It also induces the growth and the functional activation of more mature cells, including eosinophils, basophils and monocytes. The cDNA of hIL-3 has been cloned, and the mature protein of 133 amino acids has been produced in recombinant form. The human IL-3 receptor comprises at least two components, an a chain which binds IL-3 with low affinity only, and a β chain which allows high affinity binding when co-expressed with the α chain (Kitamura T, Sato N, Arak K-I and Miyajima A, 1991, Cell 66, 1165–1174).

Subsequent structure-activity relationship studies of hIL-3 have been performed by functional analysis of hIL-3 deletion and substitution variants (Lokker et al, 1991a, J. Biol. Chem. 266, 10624–10631; 1991b, EMBO J. 10, 2125–2131) using recombinant hIL-3 variants generated by site-directed mutagenesis and expression in *Escherichia coli*. In this work, the variants were analysed for their ability to bind to the IL-3 receptor and to induce the proliferation of the human IL-3 -dependent cell line M-07. These studies initially showed that hIL-3 residues Pro 33 and Leu 34 are essential for modulating the biological activity of hIL-3, and that certain substitution variants at residues 33 and 34, particularly the variant in which Pro 33 was substituted with Gly (Gly 33), showed an enhanced proliferation activity without a significant modification in its receptor binding capacity (Lokker et al, 1991a supra). Subsequent studies which extended the structure-activity- relationship studies showed that the hIL-3 residue Leu 111, and possibly also Lys 110, form part of an active site. Thus, substitution of Lys 110 with either Glu or Ala resulted in variants with substantially reduced activity in receptor binding and proliferation assays. Similarly, variants where Leu 111 was substituted by Pro or Met were totally inactive in these assays (Lokker et al, 1991b supra).

It has now been discovered that variants or mutants of hIL-3 in which one or more amino acids in or adjacent to the predicted "D" or fourth predicted α-helix of hIL-3 is/are replaced with another amino acid show enhanced biological activity when compared with wild-type hIL-3. This enhanced biological activity is paralleled by enhanced binding to the specific a chain of the IL-3 receptor, and suggests that the variants or mutants may be used as therapeutic agents.

According to a first aspect of the present invention, there is provided a human IL-3 variant or mutant, characterised in that one or more amino acids in or adjacent to the predicted "D" or fourth predicted α-helix of hIL-3 is/are replaced by another amino acid.

In one embodiment of this aspect of the invention, there is provided a human IL-3 variant or mutant, characterised in that amino acid 101 (Asp) and/or amino acid 116 (Lys) is/are replaced by another amino acid.

Particularly preferred variants or mutants in accordance with this aspect of the invention are:

hIL-3 (Ala$^{101}$)
hIL-3 (Val$^{116}$)
hIL-3 (Ala$^{101}$, Val$^{116}$)

In addition, it has also been found that replacement of one or more amino acids in the predicted "A" or first predicted α-helix with another amino acid, particularly replacement of amino acids 21, 22 and 25, results in loss of IL-3 activity to high affinity IL-3 receptors indicating that these residues form part of another IL-3 active part. It has, however, been shown that these biologically inactive mutants still retain binding ability to the α chain of the IL-3 receptor. The loss of biological activity suggests that these mutants may be used as antagonists.

According to a second aspect of this invention, there is provided a human IL-3 variant or mutant, characterised in that one or more amino acids in the predicted "A" or first predicted α-helix of hIL-3 is/are replaced by another amino acid.

In one embodiment of this aspect of the invention, there is provided a human IL-3 variant or mutant, characterised in that amino acid 21 (Asp), amino acid 22 (Glu) and/or amino acid 25 (Thr) is/are replaced by another amino acid.

Particularly preferred variants or mutants in accordance with this aspect of the invention are:

hIL-3 (Ala$^{21}$, Leu$^{22}$, Ala$^{25}$)
hIL-3 (Ala$^{21}$, Leu$^{22}$)
hIL-3 (Ala$^{21}$)
hIL-3 (Arg$^{21}$)
hIL-3 (Leu$^{22}$)
hIL-3 (Arg$^{22}$)
hIL-3 (Ala$^{25}$)

In yet another aspect, this invention provides a human IL-3 variant or mutant which is characterised in that it combines the two sets of variations or mutations broadly described above, that is amino acid replacement is effected in both the "A" α-helix and in or adjacent to the "D" α-helix. These variants or mutants will combine the antagonist activity resulting from loss of biological activity with increased affinity, resulting in enhanced IL-3 antagonist potency.

Particularly preferred variants or mutants in accordance with this aspect of the invention are:

hIL-3 (Ala$^{101}$, Val$^{116}$, Arg$^{22}$)
hIL-3 (Ala$^{101}$, Val$^{116}$, Ala$^{21}$, Leu$^{22}$)

The present invention also extends to the use of the mutants or variants as described above as therapeutic agents. Thus, these mutants or variants may be provided as active components in therapeutic compositions, together with one or more pharmaceutically acceptable carriers or diluents.

The therapeutic use of the variants or mutants of this invention may include, for example, modulation of proliferation and differentiation of haemopoietic progenitor cells or of growth and functional activation of mature haemopoietic cells. This modulation may be as an agonist or an antagonist of IL-3 function. In its broadest sense, the therapeutic use of these variants or mutants extends to modulation of the function of all cells that express or are made to express IL-3 receptor, including both haemopoietic cells and non-haemopoietic cells such as non-myeloid cells expressing or made to express IL-3 receptor.

Further details of the present invention are set out in the following Example, and in the accompanying Figures.

IN THE FIGURES:

Predicted positions of amino acid residues 101 and 116 are identified.

EXAMPLE

Materials and Methods

1. Site Directed Mutagenesis of Human IL-3

Human IL-3 mutants were constructed using either site-directed mutagenesis or the polymerase chain reaction PCR.

Substitution of amino acid residue 101 (aspartic acid) by alanine and amino acid 116 (lysine) by valine was performed by oligonucleotide site-directed mutagenesis. The method used was that of Zoller and Smith (1984, DNA, 3, 479).

The oligonucleotide sequences used were:

(a) Asp(101)-Ala:

| | | |
|---|---|---|
| SEQ ID NO:1 | 5' AT ATC AAG GCC GGT GAC TG | - native sequences |
| SEQ ID NO:2 | 3' TA TAG TTC CGG CCA CTG AC | |
| SEQ ID NO:3 | 19 mer 5' CA GTC ACC GGC CTT GAT AT | - mutant sequence |

(b) Lys(116)-Val:

| | | |
|---|---|---|
| SEQ ID NO:4 | 5' TTC TAT CTG GTG ACC CTT GAG | - native sequences |
| SEQ ID NO:5 | 3' AAG ATA GAC CAC TGG GAA CTC | |
| SEQ ID NO:6 | 21mer 5' CTC AAG GGT CAC CAG ATA GAA | - mutant sequence |

(note: altered residue(s) double underlined)

Site-directed mutagenesis involved annealing a mutagenic oligonucleotide to a single stranded M13 vector containing a hIL-3 cDNA constructed synthetically (Phillips el. al., 1989, Gene, 84, 501–507). Addition of dNTPs and DNA polymerase (Klenow fragment) allowed extension from the mutant primer along the M13 template. A primer specific for the M13 sequence (USP) was added to increase efficiency of the reaction. The resulting heteroduplex was transformed into an *E.coli* strain, JM101. Resulting plaques were lifted onto nitrocellulose filters and screened with the 32p-labelled mutagenic oligonucleotide. Single stranded DNA was prepared from positive plaques and sequenced to confirm the mutation (Zoller and Smith, supra).

A two part polymerase chain reaction was used to create mutants in the double stranded IL-3 construct, pJLA$^+$ IL-3 (Phillips et. al., supra). Three primers were involved. Two lay outside of the IL-3 gene and the third was the mutagenic oligonucleotide. In the first step the outside primer that binds to the antisense strand was used with the mutagenic oligonucleotide (binds to the sense strand). Twenty five cycles of PCR with these primers resulted in amplification of a portion of the gene. This portion contained the mutant sequence and was used as a primer together with the other outside primer (binds to the sense strand) for the second PCR reaction.

After construction of the mutants by site-directed mutagenesis or PCR, the double stranded DNA was digested with BamHI and SacI and cloned with an SacI/EcoRI cut DNA fragment containing SV40 polyadenylation signals into BamHI/EcoRI pJL4 (Gough et. al., 1985, EMBO J., 4, 645). Plasmid DNA was sequenced to confirm the presence of the IL-3 mutant sequence.

2. Transfection of IL-3 and Its Analogs.

Transient transfections were carried out in COS cells. COS cells were grown to 50–70% confluence in Dulbecco's Modified Eagle's medium (DMEM) containing 20 mM Hepes, Penicillin, Gentomycin and supplemented with 10% fetal calf serum (FCS). Cells were harvested with trypsin/EDTA, centrifuged and immediately before use resuspended in 20 mM HEPES-buffered saline containing 6 mM glucose to $1\times10^7$ cells/ml.

DNA constructs were introduced into COS cells by electroporation (Chu et. al., 1987, Nucleic Acids Res., 15, 1311–1376). For each transfection, 20 μg of pJLA$^+$ IL-3 plasmid DNA, 25 μg sonicated salmon sperm DNA and 50 μl FCS were mixed with $5\times10^6$ COS cells. The mixture was electroporated using a Bio-Rad Gene Pulser before being plated out in DMEM + 10% FCS. After a 24 hour incubation period the medium was replaced with FCS-free DMEM and incubated for a further 72 hours before the conditioned medium was harvested and assayed for IL-3 protein.

3. Visualisation of IL-3 Protein.

COS cell supernatants containing IL-3 were size-fractionated by SDS-12.5% PAGE and then protein transferred to nitrocellulose. IL-3 protein detection was carried out by Western Blot analysis using anti-human IL-3 antibodies and visualized by autoradiography after the addition of $^{125}$I-protein A.

4. Quantitation of IL-3 Protein.

The mount of IL-3 protein present in COS supernatants was quantitated by a radioimmunoassay (RIA). A competitive RIA was developed using $^{125}$-I-labelled IL-3 and a polyclonal anti-IL-3 serum (gift from Dr S Clark, Genetics Institute). IL-3 was labelled with $^{125}$I by the iodine monochloride method as described (Contreras et. al., 1983, Meth. Enzymol. 92, 277–292). COS cell supernatants (50 μl) were incubated with rabbit anti-IL-3 serum (50 μl of 1:10, 000 dilution) in Eppendorf microtubes. After 4 hr incubation at 4° C., 0.1 ng of $^{125}$I-IL-3 was added for a further 16 hr before adding 100 μl of reconstituted anti-rabbit Immunobead reagent (Bio-Rad Laboratories, Richmond, Calif.) for 4 hr. The mixtures were then washed twice with PBS, and the pellet was resuspended in 200 μl of PBS and transferred to 3DT tubes for counting in a gamma-counter (Packard Instrument Company, Meriden, Conn.). The amount of IL-3 protein was calculated from a standard curve constructed with known amounts of IL-3.

Wild type IL-3 and IL-3 (Ala$^{101}$, Val$^{116}$) protein produced in E. coli were also quantitated directly by scanning densitometry (Fazekas de St. Groth et at., 1963, Biochim. Biophys. Acta., 71,377–391). Briefly, proteins were electrophoresed on 15% SDS PAGE and stained with Coomassie brilliant blue R250. Samples of wild type IL-3, IL-3 (Ala$^{101}$, Val$^{116}$) or RNAse standards were electrophoresed over a concentration range of 0.5–5 μg in duplicate and the gel then analysed using an LKB-Pharmacia Ultrascan XL scanning laser densitometer. Data analysis was performed with GSXL densitometer software. The protein concentrations of the unknown samples were calculated using the area under the peak, relative to known amounts of RNase standards using the same absorbance coefficient. In some cases direct protein quantitation was also performed by HPLC peak integration by calculating the area under the IL-3 peak using the extinction coefficient of 0.83 AU.ml/mg. The values obtained with each method were very similar. An IL-3 preparation (gift from Genetics Institute) at 0.6 μg/ml (by amino acid analysis) measured 0.59±0.1 (mean ± SD) lag/ml by scanning laser densitometry, and 0.6±0.07 μg/ml by radioimmunoassay. In parallel, an IL-3 (Ala$^{101}$, Val$^{116}$) concentration of 1.45±0.06 μg/ml by scanning laser densitometry compared with 1.32±0.2 μg/ml by HPLC peak integration, and 1.35±0.2 μg/ml by RIA.

5. Stimulation of Hemopoietic Cell Proliferation.

Two types of assay were performed:

(a) Colony assay: this assay measured the clonal proliferation and differentiation of bone marrow progenitor cells in semi-solid agar and was carried out as described (Lopez et. al., 1985, Blood 72, 1797–1804). Briefly, low density, macrophage-depleted bone marrow cells were cultured at a concentration of 0.5 to 1×10$^5$/mL in Iscove's modified Dulbecco's medium (IMDM, GIBCI, Grant Island, N.Y.), containing 0.33% agar (Difco, Detroit), 25% FCS (Commonwealth Serum Laboratories, Parkville, Victoria, Australia), and 20 μmol/LK2-mercaptoethanol. Different dilutions of IL-3- containing COS cell supernatants were added to each plate. Plates were prepared in triplicate and scored after incubation at 37° C. in 5% CO2 in a humid atmosphere for 14 days. Clones containing 40 cells were scored as colonies.

(b) Proliferation of chronic myeloid leukaemic (CML) cells: Primarily CML cells from one patient were selected for their ability to incorporate [$^3$H] thymidine in response to IL-3 as described (Lopez el. al., supra ). Briefly, CML cells were placed at 2×10$^5$ cells/mL fresh medium containing different concentrations of IL-3. Cells were incubated for 24 hours in a flat bottom 96-well NUNCLON plates (2×10$^4$ cells/well) before being pulsed with [$^3$H] thymidine (0.5 μCi/well) for four more hours at 37° C. The cells were then harvested onto glass filters with a Titertek automated cell harvester and counted into a Beckman liquid scintillation counter. Data are expressed in cpm, and each point is the mean of six replicates.

6. Stimulation of Human Monocyte Function:

(a) Monocyte purification. Monocytes were purified from the peripheral blood of normal donors, obtained from the Adelaide Red Cross Transfusion Service, as previously described (Elliott et. al., 1990, J. Immunol., 145, 167–171). In brief, mononuclear cells were prepared by centrifugation of whole blood on lymphoprep cushions (Nyegaard, Oslo, Norway) and washed twice in HBSS, 0.02% EDTA, 0.1% heat inactivated FCS (Flow Laboratories, North Ryde, Australia) and monocytes were purified in a Beckman J-6M/E elutriator using the Sanderson chamber, a flow rate of 12 ml/min and a constant rotor speed of 2050 rpm. Cells remaining in the chamber after 30 min were collected, washed twice in HBSS, and used immediately. Using these methods, monocyte purity as assessed by morphology and nonspecific-esterase staining was always >90% and usually >95%. The major contaminating cell types were lymphocytes and granulocytes (principally basophils).

(b) Adhesion assay. Adhesion was measured by an isotopic method essentially as described (Elliott et. al., supra). In brief, purified monocytes (0.5 to 1×10$^8$) were resuspended in 1 ml RPMI 1640 with 0.1% FCS and antibiotics and incubated for 30 min at 37° C. with 500 μCi$^{51}$Cr in the form of sodium chromate (Amersham International., Buckinghamshire, England). Cells were washed thrice in RPMI 1640 and resuspended in culture medium consisting of RPMI 1640, 10% FCS, antibiotics, and 0.2% sodium bicarbonate. For measurement of adhesion, 1 to 2.5×10$^5$ monocytes were aliquotted per well in 96-well microtitre plates (Nunc, Karnstrup, Denmark) together with stimuli or control medium to a total volume of μl, and incubated for the indicated periods. Monocyte settling under these conditions were observed to be complete within 10 min of incubation. At harvest, samples of supernatant were taken to assess spontaneous $^{51}$Cr release (usually <10% of cell-associated radioactivity), wells were washed three times with RPMI 1640 at 37° C., and residual adherent cells lysed in 10 mM Tris-hydrochloride, and 1% Nonident p40 detergent (Sigma). Lysates were transferred to tubes and counted in a Packard auto-gamma 5650. Percent adherence was calculated according to the formula:

$$\% \text{ adherence} = \frac{\text{residual adherent cpm} \times 100}{\text{total cpm added} - \text{cpm spontaneously released}}$$

7. Histamine Release Assay.

This was carried out as previously described (Lopez et. al., 1990, J. Cell. Physiol., 145, 69–77). Briefly, basophils were obtained from the peripheral blood of normal individuals after dextran sedimentation and centrifugation over Lymphoprep. The percentage of basophils in these preparations varied between 0.2% and 10%. In 300 μl 2×10$^4$ cells were incubated with 2 μg/ml of purified human IgE. IgE-sensitised cells were mixed with a goat IgG antihuman IgE (Cappel 0101-0061) and rhIL-3, in a final volume of 500 μl. After incubation for 60 min at 37° C., the cells were centrifuged and 350 μl aliquots removed and stored at −20° C. before assaying for histamine content. Histamine was assayed using a radioertzymatic method essentially as described (Shaff and Beavan, 1979, Anal. Biochem., 94, 425–430). Briefly, samples of 30 μl were diluted with an equal volume of water and mixed with a 30 μl solution comprising 27.5 μl 0.1 M sodium phosphate, pH 7.9, 1.5 μl rat kidney histamine-N-methyltransferase, and 1.0 μl (0.5 μCi)$^3$H-methyl-S-adensoyl-L-methionine (Dupont Net 155, low SA). Tritium-labelled methyl-histamine was extracted into chloroform/ether, dried, and counted by scintillation spectrophotometry. The cells are expressed as nanograms of histamine per milliliter by extrapolation to a standard curve constructed with 10, 5 and 1 ng/ml of histamine (SIGMA).

8. Radioreceptor Assay:

(a) Radioiodination of hIL-3: rh IL-3 (gift from Dr. L. Park, Immunex Corporation, Seattle, Wash.) was radioiodinated by the ICI method as previously described (Contreras et. al., supra). Iodinated protein was separated from free $^{125}$I by chromatography on a Sephadex G-25 PD 10 column (Pharmacia, Uppsala, Sweden) equilibrated in phosphate-buffered saline (PBS) containing 0.02% Tween 20, and stored at 4° C. for up to 4 weeks. Before use, the iodinated protein was purified from Tween and nonprotein-associated radioactivity by cation exchange chromatography on a 0.3-ml CM-Sepharose CL-6B column (Pharmacia) and stored at 4° C. for up to 5 days. The radiolabelled IL-3 retained >90% biological activity as judged from titration curves using noniondinated rh IL-3 as controls.

(b) Competition Binding assay. Freshly purified monocytes were suspended in binding medium consisting of RPMI 1640 supplemented with 20 mmol/L/HEPES and 0.5% bovine serum albumin (BSA). Typically, equal volumes (50 μl) of 4×10$^6$ monocytes, 70 pM iodinated IL-3, and different concentrations of IL-3 and IL-3 analog were mixed in siliconised glass tubes for 16 hr at 4° C. Cell suspensions were then overlaid on 0.2 mL FCS at 4° C. and centrifuged for 30 seconds at a maximum speed in a Beckman Microfugre 12. The tip of each tube was cut off above the visible cell pellet and counted in a Packard Auto-Gamma 5650 (Downer's Grove, Ill). The results are expressed as Percent competition where 100% is the competition observed in the presence of 100 fold excess native IL-3.

9. Competitive Displacement Assay:

Human peripheral blood monocytes were used in an assay to determine the ability of mutant M37 to compete for IL-3 binding sites with wild-type IL-3. These experiments show that M37 has 10–15 fold higher affinity for the high affinity receptor on these cells than wild-type IL-3. This is reflected in the calculated dissociation constants:

WT: $K_d = 9.4 \times 10^{-12}$

M37: $K_d = 5.8 \times 10^{-13}$

10. High Affinity Binding to Cloned IL-3R α and α Chains

PolyA+ RNA was isolated from the human cord blood cell line KMT2. Oligo dT primed double stranded cDNA was synthesised and used as template for PCR amplification. The PCR primers were designed to amplify the complete coding region of the IL-3R alpha chain and also to amplify the coding region of the IL-3R α chain. The PCR products were cloned into the vector pGEM-2 for sequence verification, and then into the eukaryotic expression vector, pCDM8. The IL-3R α chain-containing plasmid was transfected into COS cells by electroporation, either on its own or in conjunction with the IL-3R α chain-containing plasmid, and after two days the cells were used for binding studies.

The binding of IL-3 (Ala$^{101}$, Val$^{116}$) produced in *E. coli* was compared to that of wild type IL-3 produced in *E. coli* and yeast in a competition assay using I$^{125}$-labelled IL-3. IL-3 (Ala$^{101}$, Val$^{116}$) was found to have 10 fold higher affinity for COS cells transfected with the IL-3R α chain cDNA and 15-fold higher affinity for COS cells transfected with the IL-3R α chain and β chain cDNAs.

RESULTS

Figure 1:
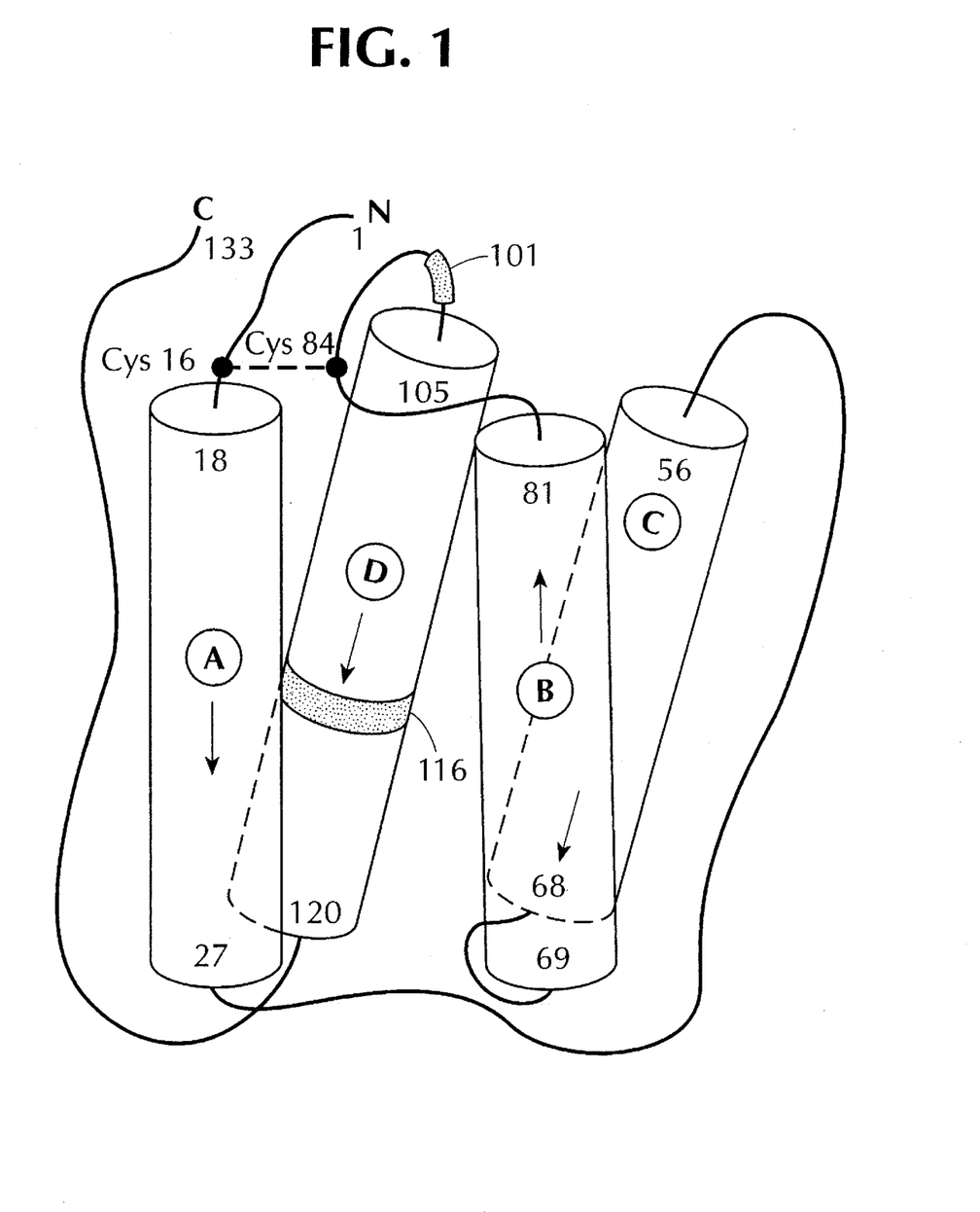
FIG. 1 shows the predicted structure of hIL-3, including the four predicted α-helix structures labelled A, B, C and D.

Mutations in the C-terminus of human IL-3 resulted in the production of three analogs: IL-3 (Ala$^{101}$) (referred to as M6); IL-3 (Val$^{116}$) (referred to as M9); and IL-3 (Ala$^{101}$, Val$^{116}$) (referred to as M37), with increased functional activity and binding (summarised in Table). The IL-3 mutant IL-3 (Ala$^{101}$, Val$^{116}$) showed the greatest increase in biological activity (15–20 fold) which correlated with increased binding affinity (16 fold). The likely location of the critical positions (101 and 116) are indicated in the predicted four alpha helical structure of IL-3 (FIG. 1) with residue 101 in a loop immediately before the predicted fourth alpha helix, and residue 116 within the predicted fourth alpha helix.

Figure 2:
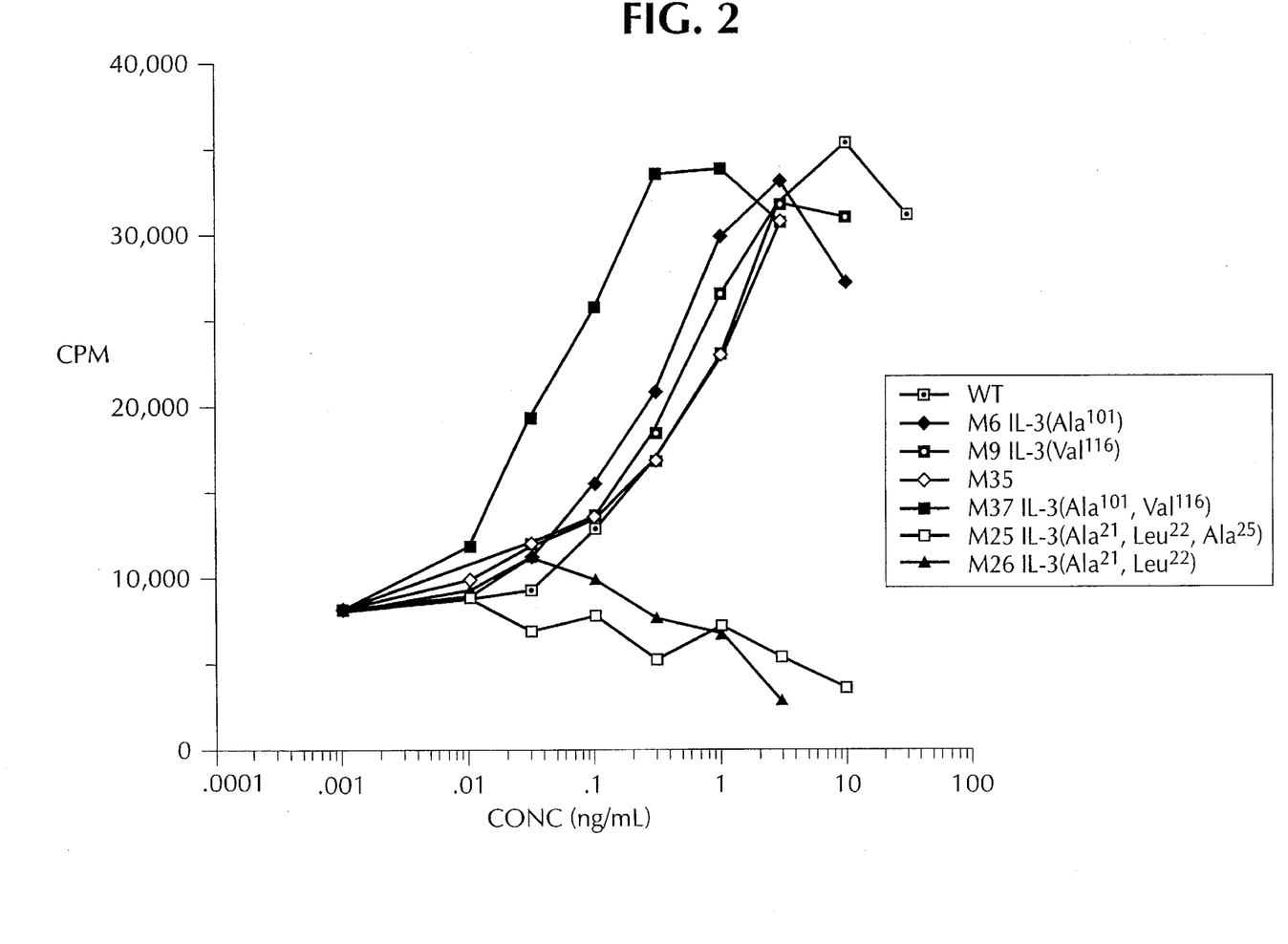
FIG. 2 shows the proliferation of chronic myeloid leukaemic (CML) cells, as measured by [$^3$H] thymidine incorporation, in the presence of different concentrations of IL-3 analogs.
Figure 4:
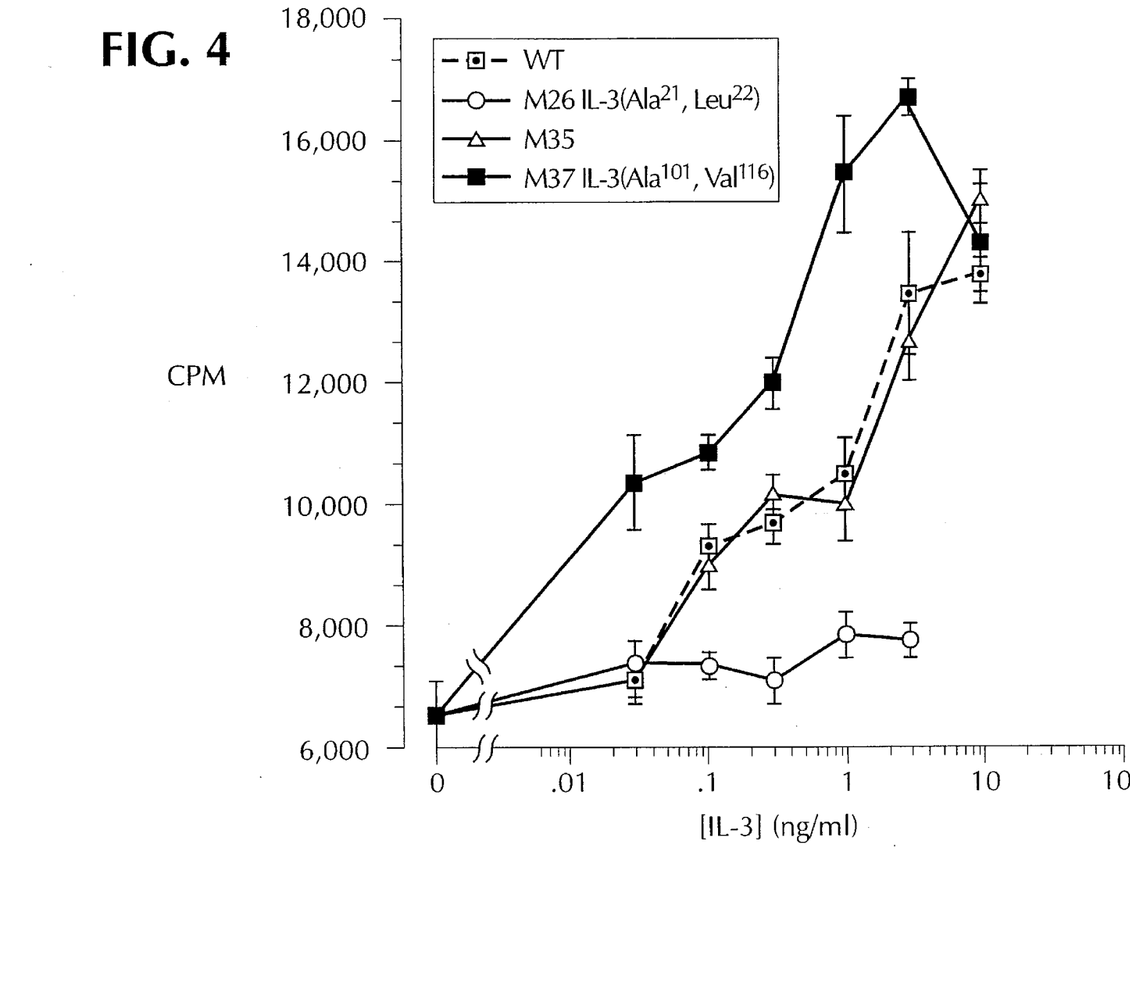
FIG. 4 shows the stimulation of histamine release by different IL-3 mutants.
Figure 5:
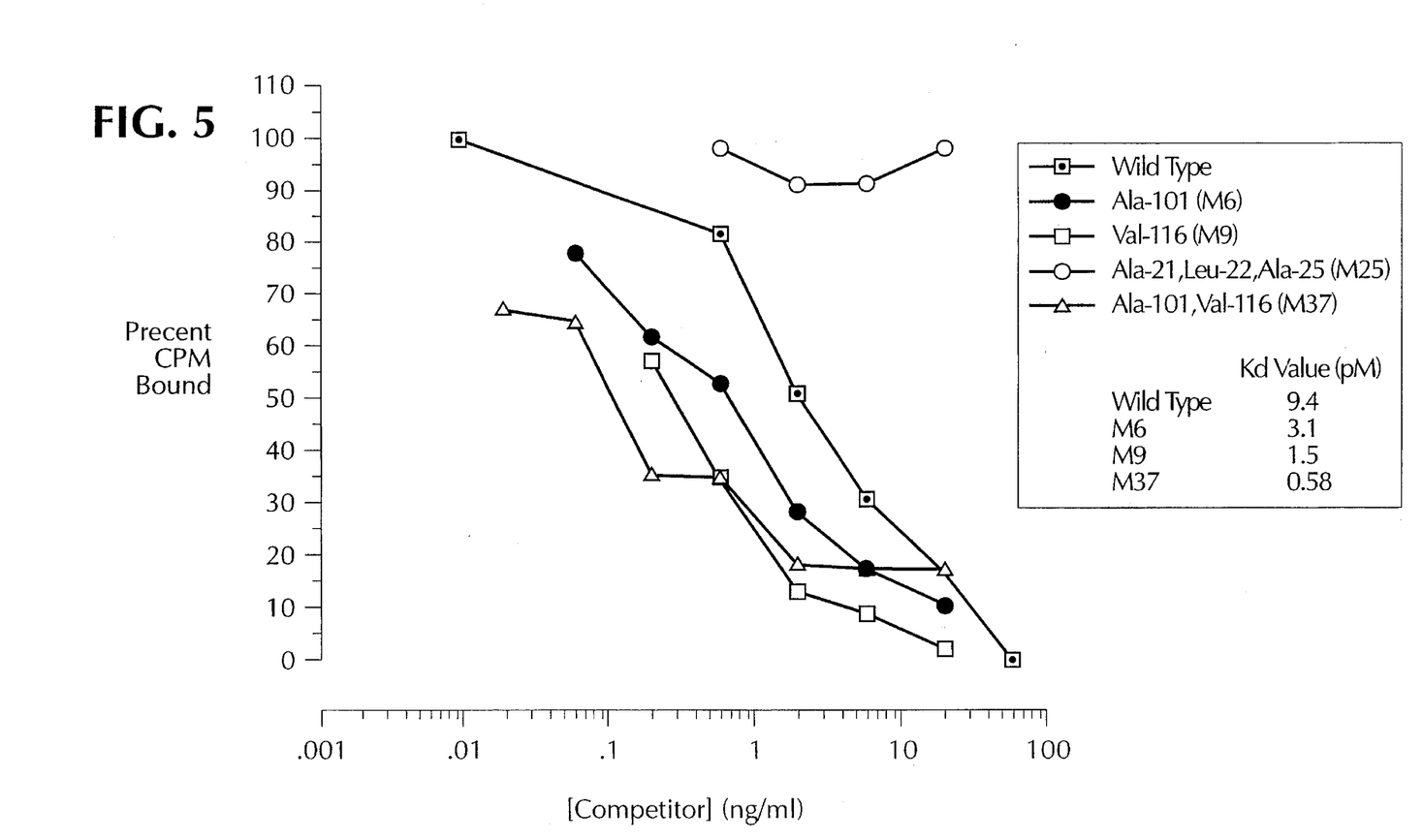
FIG. 5 shows the ability of IL-3 mutants to compete for $^{125}$I-IL-3 binding to the high affinity receptor of monocytes. The derived dissociation constants ($K_d$) for each mutant is also shown.
Figure 6:
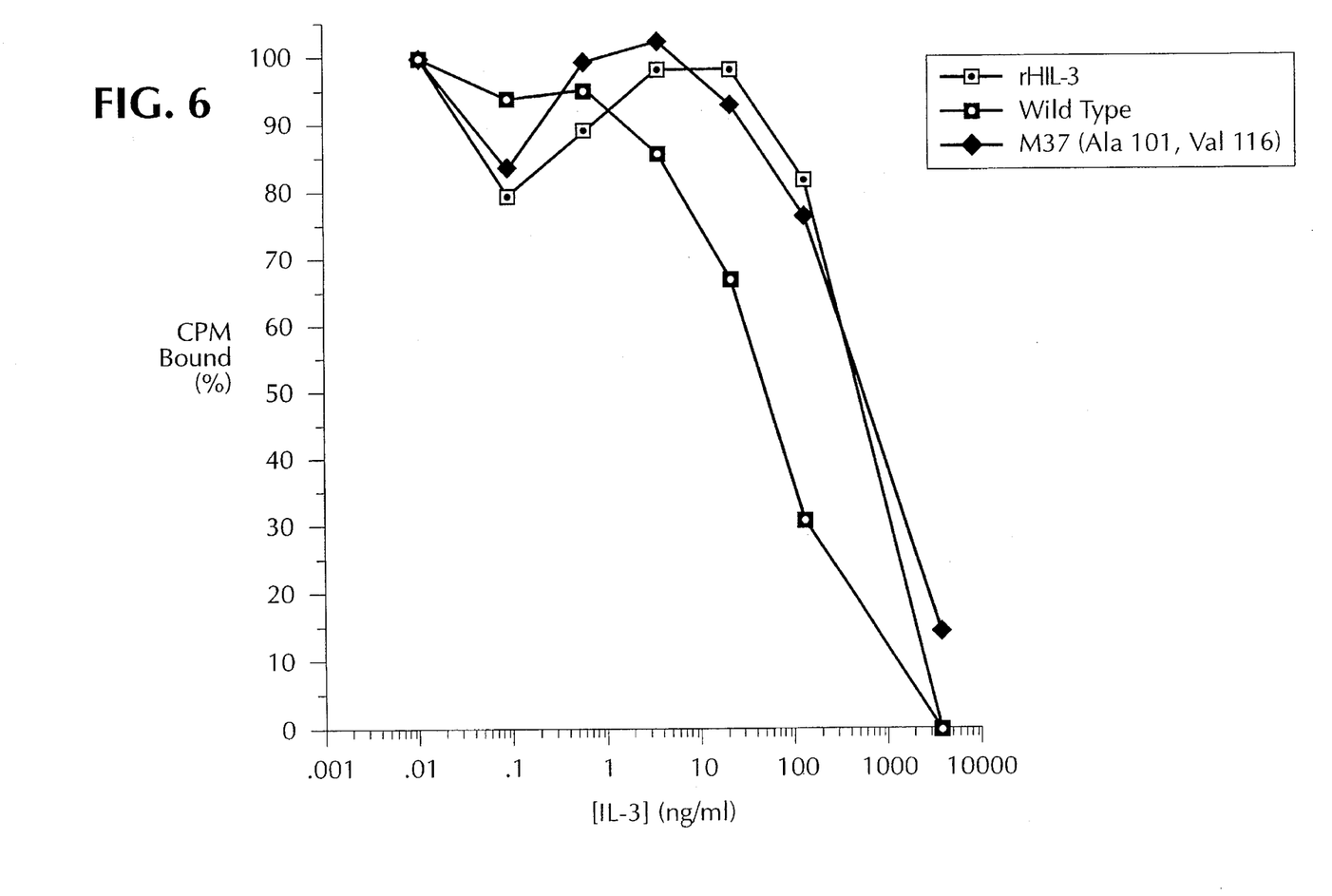
FIG. 6 shows the ability of *E. coli*IL-3 mutants to compete for $^{125}$I-IL-3 binding to the cloned IL-3R α chain expressed in COS cell transfectants. Note that IL-3 (Ala$^{101}$, Val$^{116}$) is more potent at competing for binding than wild-type IL-3.
Figure 7:
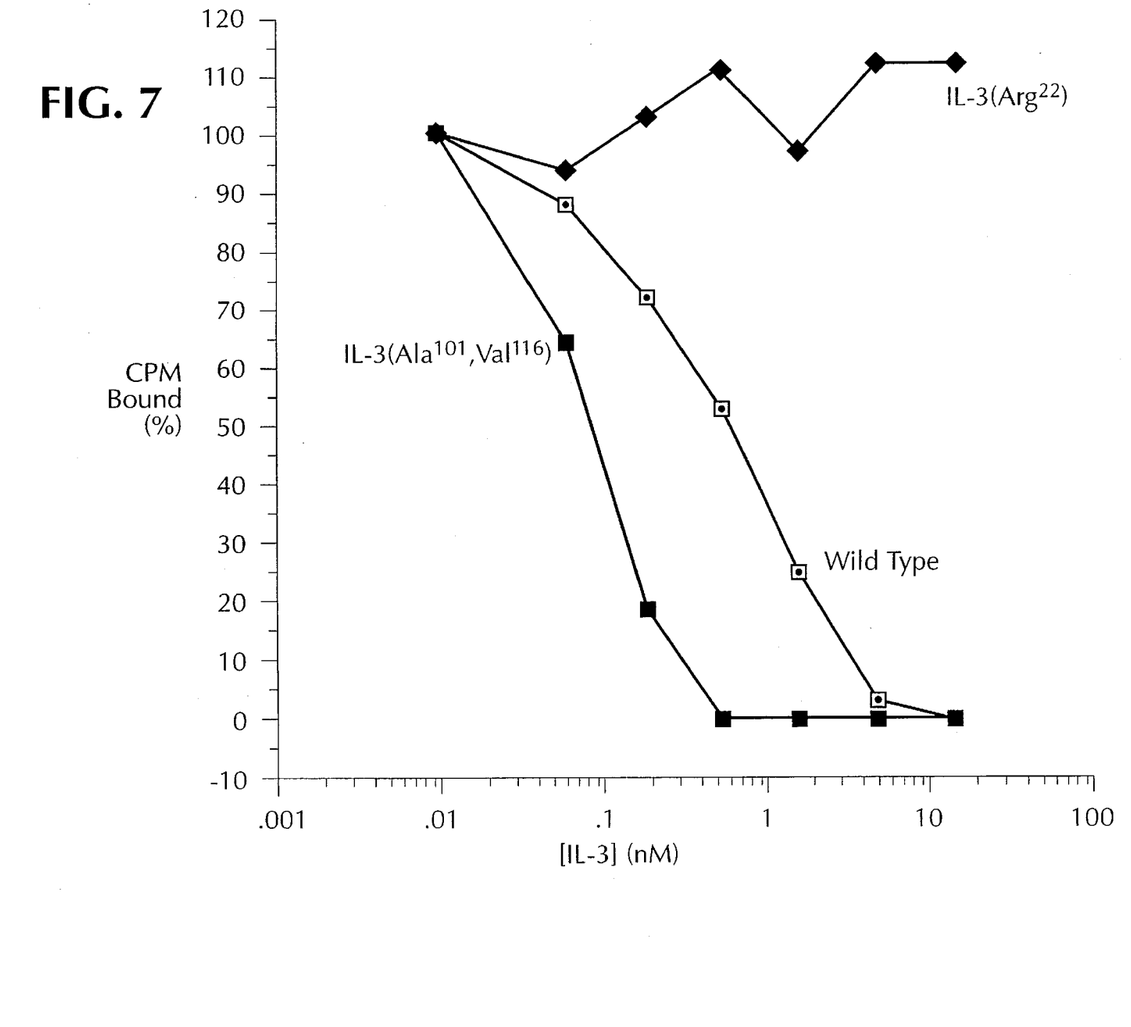
FIG. 7 shows competition of *E. coli*IL-3 mutants for $^{125}$I-IL-3 binding to the reconstituted IL-3 high affinity receptor. In this case both the cloned α and α chains were expressed in COS cells.

The increased biological activity of mutants M6, M9 and M37 is demonstrated by the stimulation of CML cells (FIG.2) and of monocyte adherence (FIG.3) where these mutants were more potent than the wild type IL-3. An increase in the number of day 14 colonies as well as increased histamine release from basophils (FIG.4) was also observed for mutants M9 and M37. The increased ability to stimulate monocyte adherence correlated with their ability to bind to the IL-3 high affinity receptor of monocytes (FIG.5) where M37 bound with a $K_d$ of 0.58 pM compared to M9 (1.5 pM), M6 (3.1 pM) and wild type IL-3 9.4 pM). The increased binding affinity was analysed on COS cells bearing the transfected IL-3 receptor α chain or both the α and β chains. As shown in FIG. 6, M37 competed for binding more efficiently to the cells expressing only the α chain, thereby demonstrating that mutation in this part of the IL-3 molecule results not only in increased potency but also in increased binding to a defined chain of the IL-3 receptor. FIG. 7 shows that M37 has higher affinity to cloned α and β chains that are cotransfected, and IL-3 (Arg$^{22}$) (referred to as M47) has less binding to the high affinity receptor obtained by cotransfecting the two chains.

Figure 3:
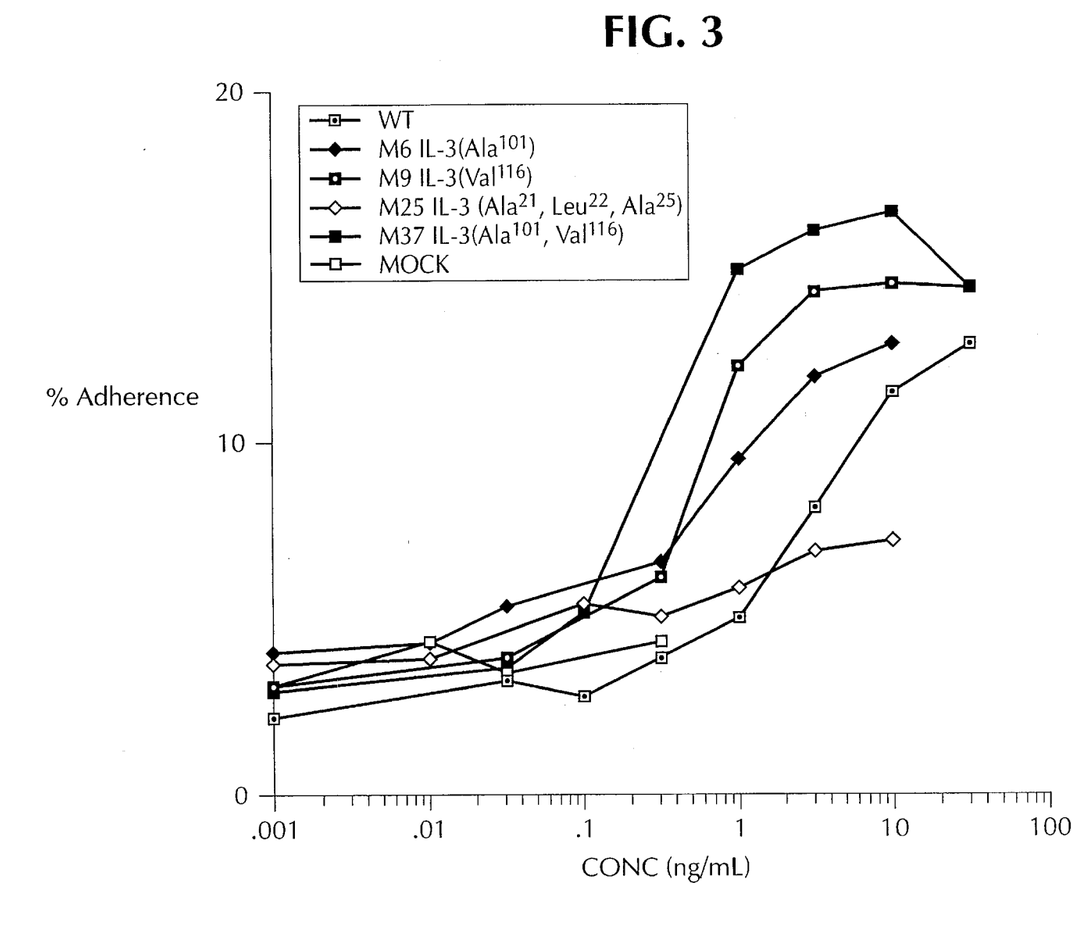
FIG. 3 shows the stimulation of monocyte adherence by different concentrations of IL-3 mutants.
Figure 8:
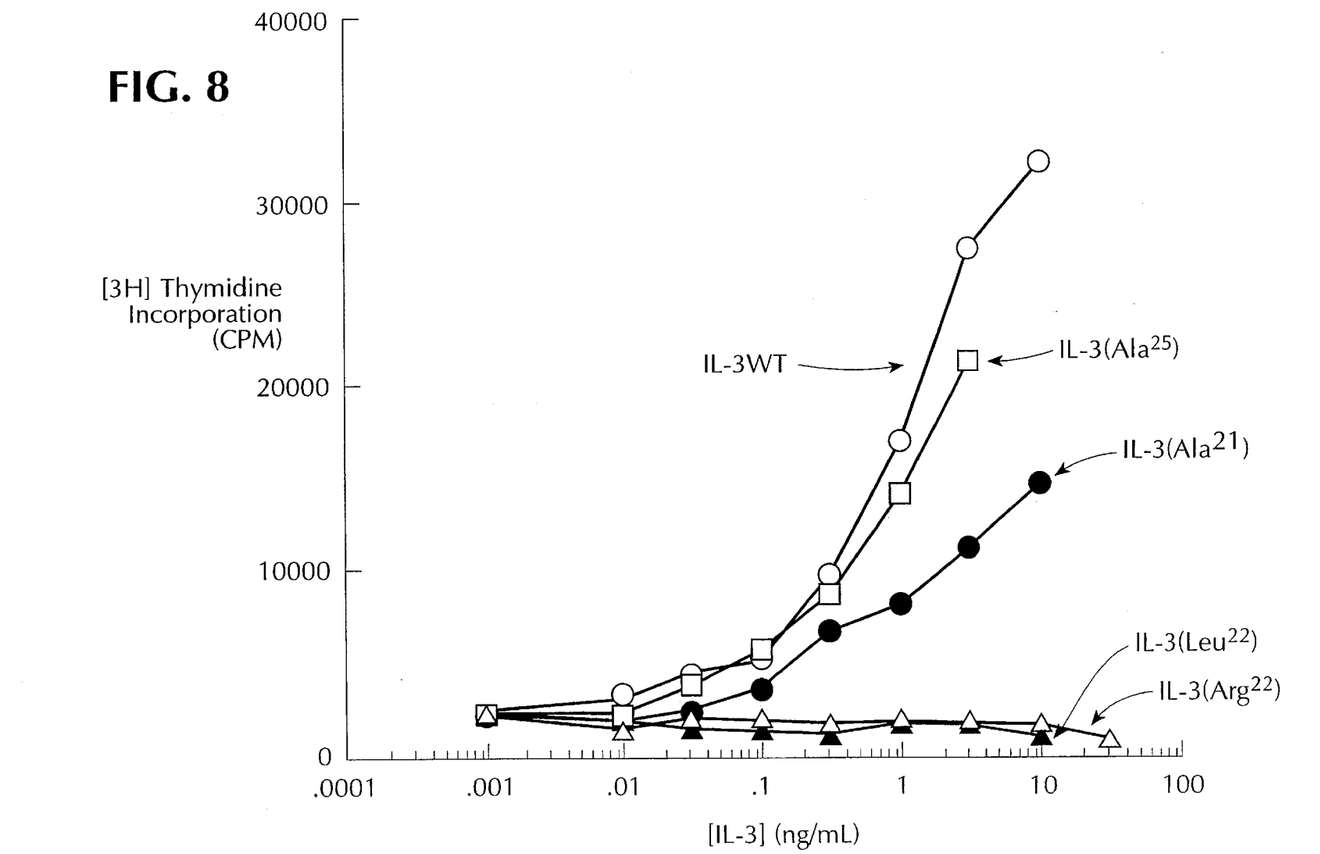
FIG. 8 shows the proliferation of chronic myeloid leukaemic cells by different IL-3 analogs. Note that replacement of glutamic acid in position 22 by leucine or arginine results in an inactive molecule.

In contrast the IL-3 mutant, IL-3 (Ala$^{21}$, Leu$^{22}$, Ala$^{25}$) (referred to as M25) showed lack of stimulation of CML proliferation (FIG.2) and of monocyte adherence (FIG.3). M25 was also negative at binding high affinity IL-3 receptors at the concentrations tested (FIG.5). These results show that M6, M9 and M37 enhance IL-3 binding as well as function, and that substitution of residues 21, 22 and 25 result in loss of agonistic function and high affinity binding. The contribution of the various mutations of M25 was analysed and the results shown in FIG. 8. It is evident that mutations at position 22 have the greatest influence on the loss of function of this mutant and mutation of glutamic acid at position 22 to arginine appears sufficient at abolishing IL-3 activity. This mutation, one that is likely to inhibit interaction with the α chain of the receptor (Lopez et al., 1992, EMBO J, 11:909–916), is a good potential basis of antagonists for IL-3 function. Furthermore combinations of M37 mutations with mutations in position 22 are likely to result in antagonists of increased affinity and therefore greater antagonist potency. Thus, the present invention includes this model of antagonist whereby two sets of mutations are introduced; one to functionally inactivate the molecule (e.g. position 22) and the other to increase its binding to one of the receptor chains (e.g. M37 mutant).

TABLE

Relative biological activity and binding affinity of IL-3 mutants

| C-TERMINAL MUTANTS | PROLIFERATION | | MONO-CYTE | BINDING Kd value (pM) + |
|---|---|---|---|---|
| | COLONIES | CML | | |
| IL-3 (Ala$^{101}$) | 104 ± 35* | 205 ± 82 | 153 ± 48 | 2.7 |
| IL-3 (Val$^{116}$) | 420 | 328 ± 116 | 312 | 1.8 |
| IL-3 (Ala$^{101}$, Val$^{116}$) | 1700 | 1694 ± 281 | 2100 | 0.58 |

*Mean ± SD of several experiments where a full titration was carried out and the concentration of IL-3-mutants giving 50% of biological activity compared to that of wild type IL-3.
+ $K_d$ of wild type IL-3 = 9.4 pM.

We claim:

1. A human IL-3 (hIL-3) variant having increased affinity, relative to native hIL-3, for the high-affinity IL-3 receptor, wherein the variations from native hIL-3 comprise the replacement of one or both of the residues $Asp^{101}$ and $Lys^{116}$ by other amino acids.

2. An hIL-3 variant according to claim 1 which retains the growth-, differentiation-, or functional activation-promoting activity of native hIL-3.

3. An hIL-3 variant according to claim 2 which is [$Ala^{101}$] hIL-3.

4. An hIL-3 variant according to claim 2 which is [$Val^{116}$] hIL-3.

5. An hIL-3 variant according to claim 2 which is [$Ala^{101}$, $Val^{116}$] hIL-3.

6. An hIL-3 variant according to claim 1 which is an antagonist of the growth-, differentiation-, or functional activation-promoting activity of native IL-3.

7. An hIL-3 variant according to claim 6, further comprising the replacement of one, two, or three of the residues $Asp^{21}$, $Glu^{22}$, and $Thr^{25}$ in native hIL-3 by other amino acids.

8. An hIL-3 variant according to claim 7 which is [$Ala^{21}$, $Leu^{22}$, $Ala^{101}$, $Val^{116}$] hIL-3.

9. A pharmaceutical composition comprising the hIL-3 variant of claim 1 and a pharmaceutically acceptable carrier or diluent.

10. A pharmaceutical composition comprising the hIL-3 variant of claim 2 and a pharmaceutically acceptable carrier or diluent.

11. A pharmaceutical composition comprising the hIL-3 variant of claim 6 and a pharmaceutically acceptable carrier or diluent.

12. A method to promote the proliferation of cells expressing a receptor for IL-3, comprising the step of contacting said cells with an effective amount of an hIL-3 variant according to claim 2.

13. A method to promote the differentiation of cells expressing a receptor for IL-3, comprising the step of contacting said cells with an effective amount of an hIL-3 variant according to claim 2.

14. A method to promote the functional activation of cells expressing a receptor for IL-3, comprising the step of contacting said cells with an effective amount of an hIL-3 variant according to claim 2.

15. A method according to any one of claims 12, 13, and 14, wherein said cells are present in a patient, and the method comprises the step of administering said variant to said patient.

16. A method to antagonize the IL-3-mediated proliferation of cells expressing a receptor for IL-3, comprising the step of contacting said cells with an effective amount of an hIL-3 variant according to claim 6.

17. A method to antagonize the IL-3-mediated differentiation of cells expressing a receptor for IL-3, comprising the step of contacting said cells with an effective amount of an hIL-3 variant according to claim 6.

18. A method to antagonize the IL-3-mediated functional activation of cells expressing a receptor for IL-3, comprising the step of contacting said cells with an effective amount of an hIL-3 variant according to claim 6.

19. A method according to any one of claims 16, 17, and 18, wherein said cells are present in a patient, and the method comprises the step of administering said variant to said patient.

\* \* \* \* \*

UNITED STATES PATENT AND TRADEMARK OFFICE
CERTIFICATE OF CORRECTION

PATENT NO.   : 5,591,427
DATED        : January 7, 1997
INVENTOR(S)  : Mathew A. Vadas et al.

Page 1 of 1

It is certified that error appears in the above-identified patent and that said Letters Patent is hereby corrected as shown below:

Column 1,
Line 2, change "va" to read as -- variants in which the amino acid --.
Line 19, change "an a chain" to read as -- an α chain --.
Line 27, change "266" to read as -- 266 --.
Line 27, change "10" to read as -- 10 --.

Column 3,
Line 23, change "α chains" to read as -- β chains --.

Column 4,
Lines 18 & 65, change "et. al.," to read as -- *et. al.*, --.
Line 21, change "and Its Analogs" to read as -- and its analogs --.
Line 60, change "mount" to read as -- amount --.
Line 63, change "Dr S Clark" to read as -- Dr. S. Clark --.

Column 5,
Line 12, change "*E. coli*" to read as -- *E. coli* --.
Line 29, change "lag/ml" to read as -- µg/ml --.
Lines 40 & 53, change "et. al.," to read as -- *et. al.*, --.

Column 6,
Lines 2 & 17, change "et. al.," to read as -- *et. al.*, --.

Signed and Sealed this

First Day of January, 2002

Attest:

*Attesting Officer*

JAMES E. ROGAN
*Director of the United States Patent and Trademark Office*